United States Patent [19]

Fukui

[11] Plant 5,243

[45] Jun. 12, 1984

[54] PEAR TREE 'GOLDEN RUSSET BOSC'

[76] Inventor: Sumio Fukui, 5335 Collins Rd., Hood River, Oreg. 97031

[21] Appl. No.: 383,116

[22] Filed: May 28, 1982

[51] Int. Cl.[3] ..... A01H 5/00

[52] U.S. Cl. ..... Plt./36

[58] Field of Search ..... Plt./36

*Primary Examiner*—James R. Feyrer

[57] ABSTRACT

As a mutation of Bosc, a new pear tree denominated 'Golden Russet Bosc' is disclosed which is characterized by the distinct, over-all orange-tinted russet formation on its fruits.

3 Drawing Figures

This discovery relates to a new and distinct variety of pear tree, and more particularly to a sport of the pear variety commonly known as the Bosc or Beurré Bosc, a variety of nonpatented pear.

This discovery was made by applicant in the year 1940 in a pear orchard which was being cultivated and maintained as a part of an operating fruit ranch near Hood River, Oreg.

Applicant's attention was attracted to the new Bosc sport tree, which at the time of its discovery had attained an age of about twelve years, by the beautiful, over-all, orange-tinged, unbroken russet formation of its fruits.

Immediate steps were taken by applicant to test the selection further and to preserve the new sport variety. Scions of the new clone were placed on pear seedling rootstocks and twelve second generation trees were propagated and planted to see if the new and distinct fruit coloring and russeting characters would transmit through to succeeding generations. Subsequently, third and fourth generation trees were propagated and planted at Hood River and at Parker, Wash.

All succeeding generations of trees illustrate that the distinctive over-all, orange-tinted russet coloring character of the pear fruits is established and has transmitted through all succeeding generations of asexual tree propagations.

In other particulars, the new sport tree is similar to the ordinary Bosc variety, i.e., the pear fruits have a shape, flesh coloring, texture, and flavor similar to that of its parent. Its over-all tree characters, i.e., leaf color and shape, tree size and tree growth characters are also similar to that of its Bosc parent.

Continued observations of the original sport tree and the progeny thereof which were derived by budding the selection onto pear seedlings and of fruit storage tests conducted using first, second, third and fourth generation fruits, established that its distinctive orange skin color and over-all russet formation were of sufficient merit to justify naming the selection, securing a patent and producing trees for sale.

BRIEF DESCRIPTION OF THE DRAWINGS

The accompanying drawing (FIG. 1) shows in full color a typical specimen of the fruit of the new variety, particularly the over-all russet spread and lack of visible yellow ground color, this being shown in comparison to its parent the common Bosc or Buerré Bosc.

Figure 1:
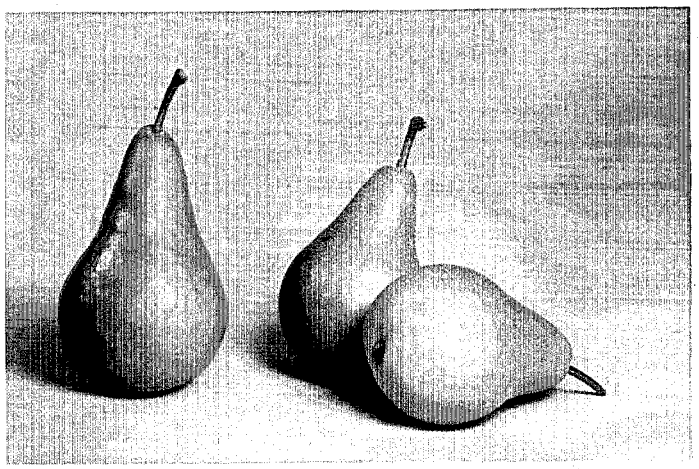
Figure 2:
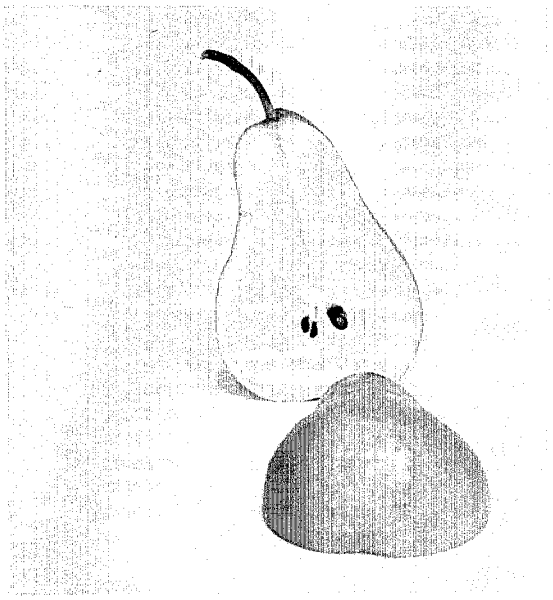
FIGS. 2 and 3 show the fruits in longitudinal and transverse cross-section respectively with seeds remaining in place and again demonstrating the complete, over-all russet character.
Figure 3:
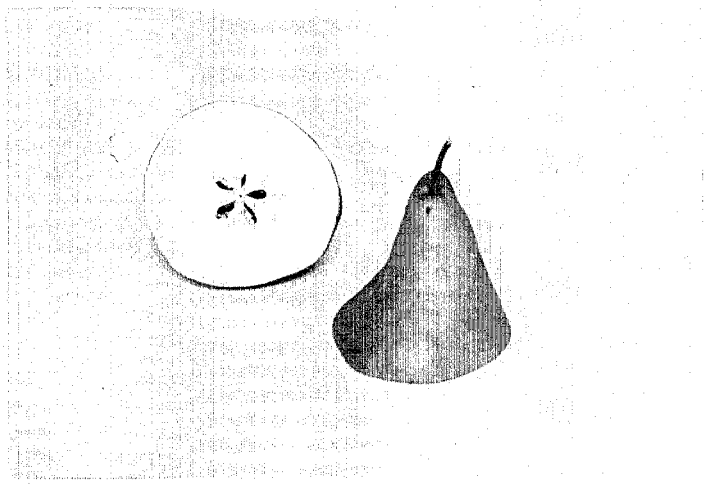

Following is a detailed description of the new variety of pear tree, such description being based upon observations of pear specimens and with reference to botanical authorities.

All major colors referred to being by reference to a Munsell Color Cascade chart except where common terms of color definition are employed.

Parentage: Whole tree sport of Bosc (Beurré Bosc).

Locality where observations were made: Hood River, Oreg. and Parker, Wash.

Tree:
- *Size.*—Medium to large.
- *Vigor.*—Consonant to Bosc.
- *Form.*—Upright-spreading.
- *Growth.*—Moderate.
- *Hardiness.*—Hardy.
- *Production.*—Very productive.
- *Bearing.*—Late; regular bearer.

Trunk:
- *Form.*—Straight.
- *Size.*—Stocky.
- *Texture.*—Medium smooth.

Branches:
- *Main branches.*—Stocky, spreading, thick, strong.
- *Lateral branches.*—Spreading, smooth, medium thick, covered with gray scarf-skin.
- *Branchlets.*—Glossy-brown tinged with gray, smooth, glabrous.
- *Lenticels.*—Large, raised, conspicuous.

Leaves:
- *Size.*—Medium, average length — 3" to 3¼". Average width — 1⅞" to 2".
- *Form.*—Ovate.
- *Apex.*—Taper-pointed.
- *Thickness.*—Medium-thick.
- *Pubescense.*—None.
- *Texture.*—Smooth, leathery.
- *Margin.*—Finely crenate.
- *Poetiole.*—Slender, medium-thick, average length — 1¼" to 1½".
- *Color.*—Topside — medium to dark green (22 - 14). Underside — lighter green (22 - 13).

Leaf-buds:
- *Form.*—Obtuse, pointed, appressed.

Leaf-scars: Prominent.

Flowers:

*Blooming period.*—In Parker, Wash. about Apr. 1st to Apr. 10th. In Hood River, Oreg. about Apr. 15th to Apr. 25th.

*Size.*—Large. Average diameter — 1½" to 1¾".

*Color.*—White, showy, in dense clusters.

*Petals.*—Obovate, broad.

*Color.*—White.

*Pedicels.*—Slightly pubescent, light green, about 1" long.

*Fertility.*—Fertile, but requires cross-pollination for crop excellency.

*Flower.*—Buds: Size — Large. Shape — Conical, pointed, free.

Fruit:

*Date of first picking.*—In Parker, Wash. about Aug. 20th. In Hood River, Oreg. about Sept. 10th.

*Date of last picking.*—In Parker, Wash. about Aug. 30th. In Hood River, Oreg. about Sept. 20th.

*Retention.*—Hangs well.

*Size.*—Large, uniform, average length — 3½" to 4". Average width — 2½" to 2¾".

*Form.*—Acute, ovate, pyriform, very long tapered neck, uniform shape symmetrical.

*Stem.*—Curved, slender, average length — 1½" to 1¾". Slightly lipped.

*Color.*—Brown over-all (29 - 14) with light green spots.

*Cavity.*—Very obtuse or lacking, occasionally very shallow and narrow, russeted, occasionally with a fleshy ring folded up around the stem and with a slight lip.

*Calyx.*—Small, open.

*Lobes.*—Persistent, short, broad, obtuse.

*Basin.*—Shallow, narrow, obtuse, smooth, round, symmetrical, russeted.

Skin:

*Texture.*—Slightly granular, tender.

*Color.* Over-all orange-tinted unbroken russet surface (31 - 14) extending to and including basin. Yellow ground color lacking. Russet streaking and russet patch effect lacking.

*Dots.*—Small, inconspicuous.

Flesh:

*Color.*—Yellowish-white (25 - 1).

*Texture.*—Slightly granular, tender, melting, buttery, juicy.

*Flavor.*—Rich, piquant, aromatic.

*Eating quality.*—Best, delicious when properly ripened.

*Core.*—Large, closed, elliptical, clasping core-lines, bluntly pointed at calyx end and very long pointed at stem end, fleshy between seeds.

*Calyx tube.*—Short, wide, conical.

*Seed.*—Wide, short, plump, obtuse.

*Color.*—Dark-brown (28 - 15).

Use: Market; dessert; shipping.

Keeping quality: Best.

Shipping quality: Best.

Resistance to insects and diseases: Similar to common Bosc; resistant to scab and mildew; subject to pear blight; medium resistance to usual pear insect pests.

Having thus disclosed my invention, I claim:

1. A new and distinct variety of pear tree as illustrated and described herein, distinguished principally from its parent, the Bosc variety, by the over-all, orange-tinted, unbroken russet formation of its fruit skin.

* * * * *